United States Patent [19]

Blyakhman

[11] Patent Number: 5,310,943
[45] Date of Patent: May 10, 1994

[54] AROMATIC TRISANHYDRIDES
[75] Inventor: Yefim Blyakhman, Bronx, N.Y.
[73] Assignee: Ciba-Geigy Corporation, Ardsley, N.Y.
[21] Appl. No.: 52,314
[22] Filed: Apr. 23, 1993

Related U.S. Application Data

[62] Division of Ser. No. 667,718, Mar. 11, 1991, Pat. No. 5,241,082.

[51] Int. Cl.$^5$ ............................................ C07D 307/77
[52] U.S. Cl. ..................................................... 549/242
[58] Field of Search .................. 549/242; 552/101, 115

[56] References Cited

U.S. PATENT DOCUMENTS

| | | | |
|---|---|---|---|
| 3,182,073 | 5/1965 | Loncrini | 260/346.3 |
| 3,182,074 | 5/1965 | Loncrini | 260/346.3 |
| 5,109,107 | 4/1992 | Vora et al. | 528/350 |

FOREIGN PATENT DOCUMENTS 1181198  11/1964  Fed. Rep. of Germany .

Primary Examiner—Bernard Dentz
Assistant Examiner—Raymond Covington
Attorney, Agent, or Firm—JoAnn Villamizar; Luther A. R. Hall

[57] ABSTRACT

Aromatic trisanhydrides of the formula (I)

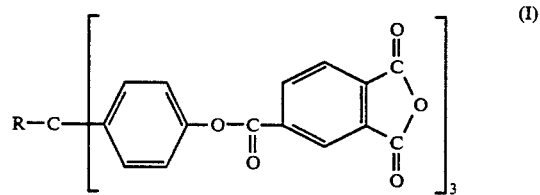

wherein R is hydrogen, $C_1$–$C_4$alkyl or aryl are useful for the synthesis of star-branched and star-burst polyester-imides and polyesterimide-amides and as curing agents for epoxy resins, phenolics and polyesters.

5 Claims, No Drawings

AROMATIC TRISANHYDRIDES

This is a divisional of Ser. No. 07/667,718, filed Mar. 11, 1991 now U.S. Pat. No. 5,241,082.

BACKGROUND OF THE INVENTION

There is a continual emphasis on improved high temperature characteristics for resinous materials and for curing agents which will improve the characteristics of already existing polymeric materials.

U.S. Pat. No. 3,182,073 describes trimellitic anhydride derivatives useful as curing agents for various resinous materials such as polyesters, epoxy resins and the like and also as substituents for preparing polyimides. U.S. Pat. No. 3,182,073 does not disclose the aromatic trisanhydrides of the present invention.

Accordingly, it is an object of the present invention to provide aromatic trisanhydrides which are useful as curing agents for epoxy resins, phenolics, polyesters and other oligomers and polymers containing hydroxyl groups and as monomer for the synthesis of star-branched polyimide-ester and polyimide-amides with radial symmetry.

It is a further object of the present invention to provide polymeric materials exhibiting high thermo-oxidative stability, Tg, toughness and mechanical strength.

Various other objects and advantages of this invention will become apparent from the following description thereof.

SUMMARY OF THE INVENTION

The present invention relates to aromatic trisanhydrides having radial symmetry for use as monomers in the synthesis of star-branched polyester-imides and polyesterimide-amides and as curing agents for epoxy resins, phenolics and polyesters.

DETAILED DESCRIPTION OF THE INVENTION

The present invention relates to aromatic trisanhydrides of the formula (I)

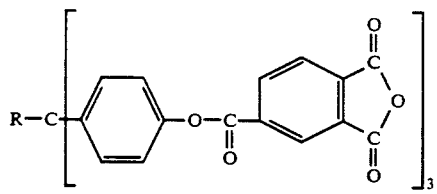

wherein R is hydrogen, $C_1-C_4$alkyl and aryl.

Aryl includes phenyl, benzyl, α-naphthyl, β-naphthyl, meta- and para-methylphenyl and trifluoromethylphenyl. Aryl is preferably phenyl. Alkyl is preferably methyl.

The trisanhydrides of this invention can be prepared by reaction of trimellitic anhydride chloride with trisphenols as exemplified in the reaction scheme below:

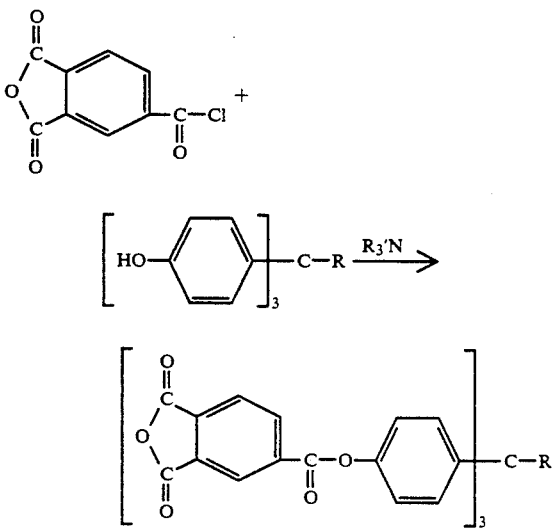

Some of the trisphenols having radial symmetry are commercially available, e.g., phloroglucinol, 1,1,1-tris(-hydroxyphenyl)-ethane. Others may be obtained by well known processes, such as condensation of phenols with compounds having the trichloromethyl group.

The preparation of the trisanhydrides according to the present invention may be carried out in anhydrous solvents, such as ether, tetrahydrofuran, acetone, methyl ethyl ketone, benzene, toluene, ethylene dichloride, etc., in the presence of tertiary amines, such as pyridine, triethylamine, etc. Preferably, the tertiary amine is added to a solution of trimellitic anhydride chloride and a tris-phenol, cooled to 0°-5° C. with subsequent stirring of the reaction mixture at 15°-75° C. for 0.5-6 hours. The resulting tris-anhydride may be separated by precipitation in a solvent in which tertiary amine hydrochlorides are soluble, such as methanol, ethanol, 2-propanol.

Multifunctional, cross-linkable polyester-imide oligomers are formed by reacting:

1) 1 mole of an aromatic trisanhydride of the formula (I),
2) 3 moles of diamine having terminal amine groups, and
3) 3 moles of an acid anhydride containing reactive groups, for example, maleimides, norbornene, etc.

The reaction is carried out by mixing the reactants in a suitable solvent in the presence of an inert atmosphere. The reaction can be exemplified in the reaction scheme below:

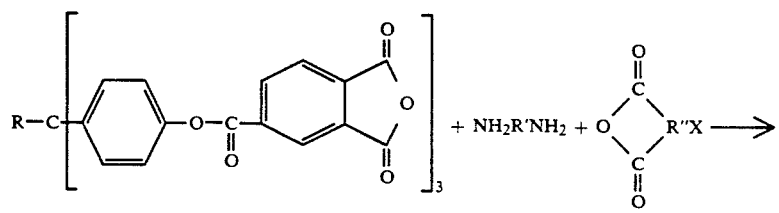

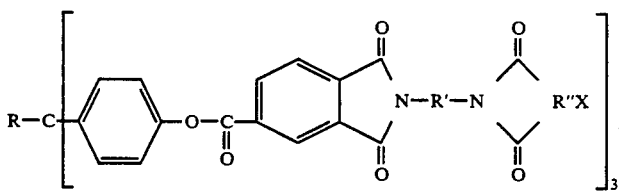

The oligomers can be crosslinked to form polymers which are processable, tough and possess excellent thermo-oxidative properties.

Suitable diamines include o-, m- and p-phenylenediamine, diaminotoluenes, such as 2,4-diaminotoluene, 1,4-diamino-2-methoxybenzene, 2,5-diaminoxylene, 1,3-diamino-4-chlorobenzene, 4,4'-diaminodiphenylmethane, 4,4'-diaminodiphenyl ether, 4,4'-diaminodiphenyl thioether, 4,4'-diaminodiphenylsulphone, 2,2'-diaminobenzophenone, 4,4'-diaminodiphenylurea and 1,8- or 1,5-diaminonaphthalene; 2,6-diaminopyridine, 2,4-diaminopyrimidine, 2,4-diamino-s-triazine, di-, tri-, tetra-, hexa-, hepta-, octa- and deca-methylenediamine, 2,2-dimethylpropylenediamine, 2,5-dimethylhexamethylenediamine, 4,4-dimethylheptamethylenediamine, 3-methylheptamethylenediamine, 3-methoxyhexamethyldiamine, 2,11-diaminododecane, 2,2,4- and 2,4,4-trimethylhexamethylenediamine, 1,2-bis-(3-aminopropoxy)ethane, N,N'-dimethylethylenediamine and N,N'-dimethyl-1,6-diaminohexane as well as the diamines of the formula $H_2N(CH_2)_3O(CH_2)_2O(CH_2)_3NH_2$ and $H_2N(CH_2)_3S(CH_2)_3NH_2$; 1,4-diaminocyclohexane, 1,4-bis-(2-methyl-4-aminopentyl)-benzene and 1,4-bis-(aminomethyl)-benzene.

Preferably, the diamine is 4,4'-diaminodiphenyl ether, 1,4-phenylenediamine or 1,3-phenylenediamine.

Suitable compounds of component (c) include 5-norbornen-endo-2,3-dicarboxyl anhydride (nadic anhydride); allyl nadic anhydride; methyl nadic anhydric, maleic anhydride and citraconic anhydride.

The preferred component (c) is 5-norbornene-endo-2,3-dicarboxyl anhydride.

Multifunctional, cross-linkable polyesterimide-amides are formed by reacting:

1) 1 mole of an aromatic trisanhydride of the formula (I),
2) 3 moles of diamine having terminal amine groups, and
3) 3 moles of an acid chloride containing reactive groups, for example, maleimides, norbornene, etc.

The reaction is carried out by mixing the reactants in a suitable solvent in the presence of an inert atmosphere. The reaction can be exemplified in the reaction scheme below:

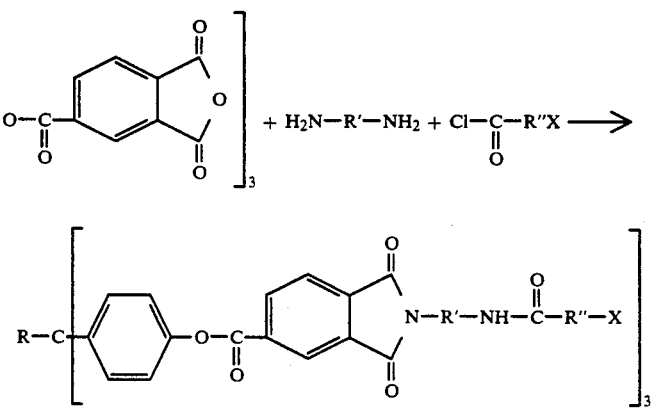

The oligomers can be crosslinked to form polymers which are processable, tough and possess excellent themo-oxidative properties.

Suitable diamines are those set forth hereinabove for the preparation of the polyester-imide oligomers.

Suitable compounds of component (c) include nadic benzoylchloride, dinadic benzoylchloride; ortho-, meta- or para-maleimido benzoic acid chloride; ortho-, meta- or para-nadicimido benzoic acid chloride and vinyl benzoic acid chloride.

The polyester-imides and polyesterimide-amides are suitable for the manufacture of shaped articles of very diverse types, such as fibres, films sheets, coating compositions, foams, laminating resins, composite materials, molding powders, pressed articles and the like, in a manner which is in itself known. The polymers according to the invention can also be processed easily from the melt and are distinguished by good mechanical, electrical and thermal properties as well as, in general, by good solubility in organic solvents, such as N,N-dimethylacetamide, N,N-dimethylformamide and N-methyl-2-pyrrolidone.

The invention further relates to a resin formulation comprising a polymer containing hydroxyl groups and an aromatic trisanhydride of the formula I described hereinabove.

The polymers useful in the formulation of the present invention include epoxy resins, phenolics and polyesters.

Suitable epoxy resins include virtually any epoxide resin having on average at least two 1,2-epoxide groups per molecule.

The following are examples of these:

I) polyglycidyl and poly-(β-methylglycidyl) esters which can be obtained, for example, by reacting a compound containing at least two carboxyl groups in the molecule with epichlorohydrin, glycerol dichlorohydrin or β-methyl epichlorohydrin in the presence of bases. Examples of compounds having at least two carboxyl groups in the molecule are saturated aliphatic dicarboxylic acids, such as oxalic acid, malonic acid, succinic acid, α-methylsuccinic acid, glutaric acid, adipic acid, pimelic acid, azelaic acid, sebacic acid or dimerized linoleic acid; or unsaturated aliphatic dicarboxylic acids, such as maleic acid, mesaconic acid, citraconic acid, glutaconic acid or itaconic acid; or cycloaliphatic dicarboxylic acids, such as hexahydrophthalic, hexahydroisophthalic or hexahydroterephthalic acid or tetrahydrophthalic, tetrahydroisophthalic or tetrahydroterephthalic acid or 4-methyltetrahydrophthalic acid, 4-methylhexahydrophthalic or endomethylenetetrahydrophthalic acid; or aromatic dicarboxylic acids, such as phthalic, isophthalic or terephthalic acid; or copolymers of meth(acrylic acid with copolymerizable vinyl monomers, for example the 1:1 copolymers of methacrylic acid with styrene or with methyl methacrylate. Examples of tricarboxylic and higher carboxylic acids are especially aromatic tricarboxylic or tetracarboxylic acids, such as trimellitic acid, trimesic acid, pyromellitic acid or benzophenonetetracarboxylic acid, and also dimerized or trimerized fatty acids such as are available commercially, for example, under the name Pripol ®.

II) Polyglycidyl and poly-(β-methylglycidyl) ethers which can be obtained, for example, by reacting a compound containing at least two alcoholic hydroxyl groups and/or phenolic hydroxyl groups in the molecule with epichlorohydrin, glycerol dichlorohydrin or β-methyl epichlorohydrin under alkaline conditions or in the presence of an acid catalyst with subsequent treatment with alkali. Examples of compounds having at least two alcoholic hydroxyl groups and/or phenolic hydroxyl groups in the molecule are aliphatic alcohols, such as ethylene glycol, diethylene glycol and higher poly-(oxyethylene) glycols, propane-1,2-diol, propane-1,3-diol or higher poly-(oxypropylene) glycols, butane-1,4-diol or higher poly-(oxybutylene) glycols, pentane-1,5-diol, neopentyl glycol (2,2-dimethylpropanediol), hexane-1,6-diol, octane-1,8-diol, decane-1,10-diol or dodecane-1,12-diol; hexane-2,4,6-triol, glycerol, 1,1,1-trimethylolethane, 1,1,1-trimethylolpropane, pentaerythritol, sorbitol or polyepichlorohydrins; or cycloaliphatic alcohols, such as 1,3-dihydroxycyclohexane, 1,4-dihydroxycyclohexane, 1,4-cyclohexanedimethanol, bis-(4-hydroxycyclohexyl)-methane, 2,2-bis-(4-hydroxycyclohexyl)-propane or 1,1-bis-(hydroxymethyl)-cyclohex-3-ene; or alcohols containing aromatic groups, such as N,N-bis-(2-hydroxyethyl)-aniline or p,p'-bis-(2-hydroxyethylamino)-diphenylmethane; or mononuclear or polynuclear polyphenols, such as resorcinol, hydroquinone, bis-(4-hydroxyphenyl)-methane, 2,2-bis-(4-hydroxyphenyl)-propane, brominated 2,2-bis-(4-hydroxyphenyl)-propane, bis-(4-hydroxyphenyl) ether, bis-(4-hydroxyphenyl) sulfone, 1,1,2,2-tetrakis-(4-hydroxyphenyl)-ethane or novolaks which are obtainable by the condensation of aldehydes, such as formaldehyde, acetaldehyde, chloral or furfuraldehyde, with phenols which are unsubstituted or substituted by alkyl or halogen, such as phenol, the bisphenols described above, 2-methylphenol, 4-methylphenol, 4-tert-butylphenol, p-nonylphenol or 4-chlorophenol.

III) Poly-(N-glycidyl) compounds which can be prepared, for example, by dehydrochlorinating reaction products of epichlorohydrin with amines containing at least two amino hydrogen atoms. Examples of amines on which such epoxy resins are based are aliphatic amines, such as hexamethylenediamine or n-butylamine; cycloaliphatic amines, such as 1,4-diaminocyclohexane or bis-aminomethylene-1,4-cyclohexane; aromatic amines, such as aniline, p-toluidine, bis-(4-aminophenyl)-methane, bis-(4-aminophenyl) ether, bis-(4-aminophenyl) sulfone, 4,4'-diaminobiphenyl or 3,3'-diaminobiphenyl; or araliphatic amines, such as m-xylylenediamine. The poly-(N-glycidyl) compounds also include, however, triglycidyl isocyanurate, N,diglycidyl derivatives of cycloalkyleneureas, such as ethyleneurea or 1,3-propyleneurea, and N,diglycidyl derivatives of hydantoins, such as 5,5-dimethylhydantoin.

IV) Poly-(S-glycidyl) compounds, for example di-S-glycidyl derivatives derived from dithiols, such as ethane-1,2-dithiol or bis-(4-mercaptomethylphenyl) ether.

V) Cycloaliphatic epoxy resins or epoxidation products of dienes or polyenes, such as cycloaliphatic epoxy resins which can be prepared, for example, by epoxidation of ethylenically unsaturated cycloaliphatic compounds. Examples of these are 1,2-bis-(2,3-epoxycyclopentyloxy)-ethane, 2,3-epoxycyclopentyl glycidyl ether, diglycidyl cyclohexane-1,2-dicarboxylate, 3,4-epoxycyclohexyl glycidyl ether, bis-(2,3-epoxycyclopentyl) ether, bis-(3,4-epoxycyclohexyl) ether, 5(6)-glycidyl-2-(1,2-epoxyethyl)-bicyclo[2.2.1]heptane, dicyclopentadiene dioxide, cyclohexa-1,3-diene, 3,4-epoxy-6-methylcyclohexylmethyl 3',4'-epoxy-6'-methylcyclohexanecarboxylate or 3,4-epoxycyclohexylmethyl 3',4'-epoxycyclohexanecarboxylate. It is also possible, however, to use epoxy resins in epoxycyclohexanecarboxylate. It is also possible, however, to use epoxy resins in which the 1,2-epoxy groups are attached to various heteroatoms or functional groups; such compounds include, for example, the N,N,O-triglycidyl derivative of 4-aminophenol, the N,N,O-triglycidyl derivative of 3-aminophenol, the glycidyl ether/glycidyl ester of salicylic acid, N-glycidyl-N'-(2-glycidyloxypropyl)-5,5-dimethylhydantoin or 2-glycidyloxy-1,3-bis-(5,5-dimethyl-1-glycidylhydantoin-3-yl)-propane.

Preferred epoxy resin are Bishpenol A diglycidyl ethers, N,N'-tetraglycidyl diamines, glycidyl ethers of phenolaldehyde condensates.

Suitable phenolic resins are those obtained by the condensation of phenol or substituted phenols. With aldehydes such as formaldehyde, acetaldehyde and furfuraldehyde. Examples of phenols and substituted phenols are phenol, alkyl-substituted phenols, including cresols, xylenols, p-tert-butylphenol, p-phenylphenol, and nonylphenol. Preferred is the condensation product of phenol and formaldehyde.

Suitable polyesters are those which are derived from dicarboxylic acids and diols and/or from hydrocarboxylic acids or the corresponding lactones, such as polyethylene terephthalate, polybutylene terephthalate, poly-1,4-dimethylol-cyclohexane terephthalate, polyhydroxybenzoates as well as block-copolyetheresters derived from polyethers having hydroxyl end groups.

The epoxy resin formulations of the present invention comprise about 30 to about 80 parts by weight of epoxy resin and about 70 to about 20 parts by weight of an aromatic trisanhydride of the formula I described hereinabove.

The polyester resin formulations of the present invention comprise about 70 to about 90 parts by weight of a polyester resin and from about 30 to about 1, preferably about 10 to about 5 parts by weight of an aromatic trisanhydride of formula I described hereinabove.

The amount of the resin and the trisanhydride will vary with the particular resin and aromatic trisanhydride chosen. The exact formulation for each is well within the ambit of the skilled artisan based on the guidance provided herein.

The compositions of the invention may also contain other conventional modifiers such as extenders, fillers and reinforcing agents, pigments, dyestuffs, organic solvents, plasticizers, tackifiers, rubbers, diluents, latent curing agents and the like. As extenders, reinforcing agents, fillers and pigments which can be employed in the compositions according to the invention there may be mentioned, for example: glass fibers, glass balloons, boron fibers, carbon fibers, cellulose, polyethylene powder, polypropylene powder, mica, asbestos, quartz powder, gypsum, antimony trioxide, bentones, talc, silica aerogel ("Aerosil"), fumed silica, lithopone, barite, calcium carbonate, titanium dioxide, carbon black, graphite, iron oxide, or metal powders such as aluminum powder or iron powder. The preferred fillers are glass balloons and fumed silica. The preferred latent curing agent is dicyandiamide. It is also possible to add other usual additives, for example, agents for conferring thixotropy, flow control agents such as silicones, cellulose acetate butyrate, polyvinyl butyral, stearates and the like.

A vertical type high-speed agitator, kneading machine, roll machine, ball mill or any other suitable mixing and agitating machine may be used for dispersion of the components of the composition of the present invention.

The resin compositions in accordance with the present invention are particularly useful for the preparation of structures for the aerospace industry.

The following examples serve to give specific illustrations of the practice of this invention but they are not intended in any way to limit the scope of this invention.

EXAMPLE 1

Synthesis of the Trisanhydride I

To the solution of 12.6 g (0.1 mol) of anhydrous phloroglucinol and 63.2 g (0.3 mol) of trimellitic anhydride chloride in 300 ml of dry acetone cooled to 0° C. under $N_2$ 26.1 g of dry pyridine (0.3 m+10% excess) was added dropwise (~1 hour). Afterwards, the reaction mixture was stirred at room temperature for 2 hours and at 50°–55° C. for 0.5 hour. After cooling to RT, the mixture was added to 1.5 liters of dry isopropanol, whereupon a fine white precipitate was formed which was washed sequentially with methanol and ether, then dried in vacuum overnight at 110° C. The product—an off-white powder—had a melting point of 299°–300° C. A yield of 58 g (90%) was obtained. Elemental analysis: calculated for $C_{33}H_{12}O_5$C: 61.1%, H 1.8%; found: C 60.7%, H 1.6%. Structure of the trisanhydride was also confirmed by IR and NMR.

EXAMPLE 2

Synthesis of the Trisanhydride II (R—$CH_3$)

To the solution of 30.6 g (0.1 mol) of 1,1,1-Tris(4-hydroxyphenyl)ethane and 63.2 g (0.3 mol) of trimellitic anhydride chloride in 400 ml of dry tetrahydrofuran cooled to 2° C. under $N_2$ 34 g of triethylamine was added dropwise (~1 hour). After that, the reaction mixture was stirred at RT for 6 hours and precipitated in 2 liters of dry isopropanol. The precipitate was washed with methanol and ether. The product—an off-white powder—had a melting point of 301°–302° C. A yield of 78.5 g (95%) was obtained. Elemental analysis: calculated for $C_{47}H_{24}O_{15}$: C 68.1%, H 2.8%; found: C 67.5%, H 2.5%.

EXAMPLE 3

Synthesis of Star Branched Aromatic Polyester-imide Based on Trisanhydride I

To the solution of 64.8 g (0.1 mol) of the trisanhydride I and 49.2 g (0.3 mol) of 5-norbornene-endo-2,3-dicarboxyl anhydride in 500 ml of dry dimethylacetamide (DMAC) cooled to 0° C. under $N_2$ the solution of 60 g (0.3 mol) of 4-aminophenylether in 500 ml of DMAC was added dropwise (3 hours) and the reaction mixture was stirred at room temperature overnight. Then 300 ml of toluene were added and the mixture refluxed until the water was completely eliminated. Toluene was distilled off and the solution stirred at 150°–155° C. for 6 hours. After cooling, the solution was precipitated in 5 liters of cold water. The precipitate—yellow powder—was washed with water 3 times and dried in vacuum at 80° C. The formation of the imide structure in the product was confirmed by the presence of characteristic absorptions in IR spectra at 1783, 1375 and 717–721 cm$^{-1}$. The absorption band at 1748 cm$^{-1}$ may be due to overlapping of the absorptions from the imide structure and the ester group. The oligomer formed a clear melt at 230°–235° C. and underwent an exothermic polymerization process at 310°–320° C.

EXAMPLE 4

Synthesis of Star Branched Polyester-imide Based on the Trisanhydride II (R=$CH_3$)

To the solution of 32.4 g (0.3 mol) of 1,3-phenylenediamine in 750 ml of N-methylpyrrolidinone cooled to 0° C. under $N_2$ the mixture of 82.8 g (0.1 mol) of the trisanhydride II (R—$CH_3$) and 49.2 g (0.3 mol) of 5-norbornene-endo-2,3-dicarboxylic anhydride was added in 6 portions (3 hours) and the reaction mixture was stirred at RT overnight. After that, 500 ml of toluene were added and the solution refluxed until all the water was eliminated. Toluene was distilled off and the solution stirred at 160° C. for 6 hours. After cooling, the solution was precipitated in 6 liters of ice-water mixture. The precipitate was washed with water and dried in a vacuum oven at 110° C. IR of the product was similar to that described in Example 3. The obtained unsaturated ester-imide oligomer formed a clear melt at 240°–250° C. and underwent polymerization at 315°–320° C.

EXAMPLE 5

Curing of an Epoxy Resin with the Trisanhydride I 10 g of the Bisphenol A based epoxy resin 6010 (CIBA-GEIGY) having an epoxy equivalent of 190 were mixed with 12.5 g of the trisanhydride I. According to DSC data, the crosslinking reaction started at 140° C. and had the peak temperature of 180° C. The mixture was cured at 150° C. for 1 hour, 180° C. for 2 hours and 220° C. for 5 hours. The cured resin showed no glass transition (DSC) upon heating to 350° C.

EXAMPLE 6

Synthesis of Polyester-imide-amide

To a solution of 64.8 g (0.1 mol) of the trisanhydride I of Example 1 in 500 ml of dry DMAC cooled to 0° C. under N₂, a solution of 60 g (0.3 mol) of 4-aminophenylether in 500 ml of dry DMAC was added dropwise (3 hrs). Then, a solution of 100.5 g (0.3 mol) of 4-nadicimido benzoic acid chloride in 600 ml of dry DMAC was added dropwise (5 hrs) at 0° C. and the reaction mixture stirred at room temperature overnight. Then, 500 ml of toluene was added and the mixture refluxed until the water was eliminated. Toluene was then distilled off and the solution stirred at 150°-155° C. for 4 hours. After cooling, the solution was precipitated in 5 liters of cold water. The precipitate—yellow powder—was washed with water 3 times and dried under vacuum at 80° C. The formulation of the amide-imide-ester structure in the product was confirmed by the presence of the characteristic absorptions in the IR spectra at 3300, 3050, 1783, 1748, 1375 and 717–721 cm$^{-1}$. The oligomer formed a clear melt at 220°-230° C. and underwent an exothermic polymerization process at 310°-320° C.

Polymer structure:

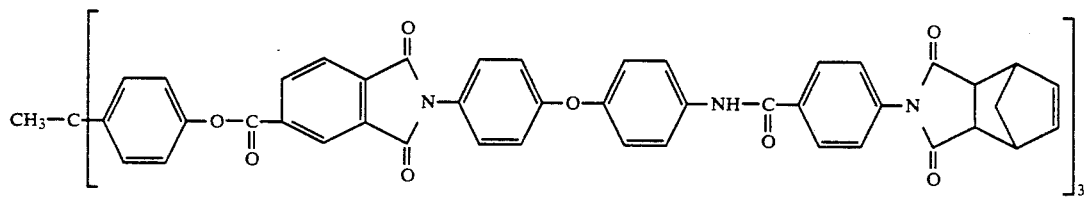

What is claimed is:

1. An aromatic trisanhydride of formula (I)

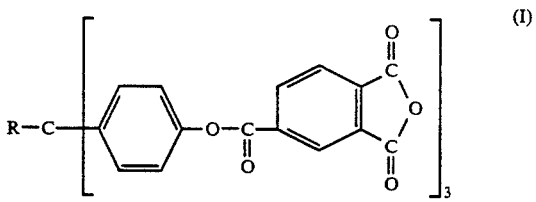

wherein R is hydrogen, C₁–C₄alkyl or aryl.

2. An aromatic trisanhydride according to claim 1 wherein R is aryl.

3. An aromatic trisanhydride according to claim 2 wherein R is selected from the group consisting of phenyl, benzyl, α-naphthyl, β-naphthyl, meta- and para-methylphenyl and trifluoromethylphenyl.

4. An aromatic trisanhydride according to claim 3 wherein R is phenyl.

5. An aromatic trisanhydride according to claim 1 wherein R is methyl.

* * * * *